US012613214B2

(12) United States Patent
Ertl et al.

(10) Patent No.: US 12,613,214 B2
(45) Date of Patent: Apr. 28, 2026

(54) METHOD FOR DETECTING AND QUANTIFYING ANALYTES IN A MICROFLUIDIC DEVICE

(71) Applicant: Technische Universität Wien, Vienna (AT)

(72) Inventors: Peter Ertl, Vienna (AT); Syed Faheem Ali, Vienna (AT); Silvia Schobesberger, Vienna (AT); Selina Schweinberger, Vienna (AT)

(73) Assignee: Technische Universität Wien, Vienna (AT)

( * ) Notice: Subject to any disclaimer, the term of this patent is extended or adjusted under 35 U.S.C. 154(b) by 625 days.

(21) Appl. No.: 18/017,058

(22) PCT Filed: Aug. 4, 2021

(86) PCT No.: PCT/EP2021/071738
§ 371 (c)(1),
(2) Date: Jan. 19, 2023

(87) PCT Pub. No.: WO2022/029160
PCT Pub. Date: Feb. 10, 2022

(65) Prior Publication Data
US 2023/0296551 A1      Sep. 21, 2023

(30) Foreign Application Priority Data
Aug. 4, 2020    (EP) .................................... 20189436

(51) Int. Cl.
*G01N 27/327*      (2006.01)
*B01L 3/00*        (2006.01)
(Continued)

(52) U.S. Cl.
CPC .... *G01N 27/3276* (2013.01); *B01L 3/502761* (2013.01); *G01N 27/3278* (2013.01);
(Continued)

(58) Field of Classification Search
None
See application file for complete search history.

(56) References Cited

U.S. PATENT DOCUMENTS

2009/0221431 A1    9/2009  Yoo
2016/0238553 A1    8/2016  Shachar
(Continued)

FOREIGN PATENT DOCUMENTS

WO      2016/129894 A1    8/2016
WO      2018/170156 A1    9/2018
WO      WO-2019084051 A1 *  5/2019    ......... G01N 33/5695

OTHER PUBLICATIONS

Dector et al. (J. Power Sources; v288, 2015, pp. 70-75) (Year: 2015).*
(Continued)

*Primary Examiner* — Kevin M Bernatz
(74) *Attorney, Agent, or Firm* — Workman Nydegger

(57)      ABSTRACT

Microfluidic device (1) comprising at least one fluid channel (2) comprising at least one inlet (3), wherein said at least one fluid channel (2) is fluidly connected to a first sensor (4) downstream of said at least one fluid inlet (3), wherein the first sensor (4) comprises at least one sensor cathode (5) and at least one sensor anode (6) formed on an essentially electrically isolating substrate (7), wherein the sensor cathode (5) and the sensor anode (6) are spaced apart by a gap (8) formed on the electrically isolating substrate (7), and wherein at least one analyte capturing molecule (9) is immobilized in the gap (8) on the substrate (7), wherein the
(Continued)

at least one capturing molecule (9) is adapted to capture at least one analyte (10) of a fluid sample introduced into the inlet (3) and transported to the first sensor (4).

29 Claims, 7 Drawing Sheets

(51) Int. Cl.

| | |
|---|---|
| *G01N 33/543* | (2006.01) |
| *G01N 33/569* | (2006.01) |
| *H01M 8/16* | (2006.01) |
| *H01M 8/2455* | (2016.01) |

(52) U.S. Cl.
CPC ... *G01N 33/5438* (2013.01); *G01N 33/56983* (2013.01); *H01M 8/16* (2013.01); *H01M 8/2455* (2013.01); *B01L 2200/0652* (2013.01); *B01L 2200/16* (2013.01); *B01L 2300/0645* (2013.01); *B01L 2300/0883* (2013.01); *G01N 2469/10* (2013.01)

(56) References Cited

U.S. PATENT DOCUMENTS

| | | | |
|---|---|---|---|
| 2019/0025241 A1 | 1/2019 | Hwang et al. | |
| 2021/0069713 A1* | 3/2021 | Civelekoglu | ............. B03C 1/01 |
| 2024/0192163 A1* | 6/2024 | Meier | ............... B01L 3/502753 |

OTHER PUBLICATIONS

Lim et al. (Biosensors and Bioelectronics; v22(6), 2006, pp. 941-971) (Year: 2006).*

Bazylak, A. et al., "Improved fuel utilization in microfluidic fuel cells: A computational study", Journal of Power Sources, vol. 143, No. 1-2, Apr. 27, 2005, pp. 57-66.

Dector, A. et al., "Perspective use of direct human blood as an energy source in air-breathing hybrid microfluidic fuel cells", Journal of Power Sources, vol. 288, Apr. 22, 2015, pp. 70-75.

Dector, A. et al., "Towards autonomous lateral flow assays: Paper-based microfluidic fuel cell inside an HIV-test using a blood sample as fuel", International Journal of Hydrogen Energy, vol. 42, No. 46, Jul. 26, 2017, pp. 27979-27986.

International Search Report and Written Opinion received for PCT Patent Application No. PCT/EP2021/071738, mailed on Mar. 21, 2022, 18 pages.

Invitation to Pay Additional Fees received for PCT Patent Application No. PCT/EP2021/071738, mailed on Nov. 9, 2021, 12 pages.

Lim et al., "Microfluidic biofuel cells The influence of electrode diffusion layer on performance", Biosensors and Bioelectronics, vol. 22, No. 6, Dec. 14, 2006, pp. 941-947.

Yang, W. et al., "A laminar-flow based microbial fuel cell array", Sensors and Actuators B: Chemical vol. 243, Nov. 30, 2016, pp. 292-297.

* cited by examiner

Covalent binding

METHOD FOR DETECTING AND QUANTIFYING ANALYTES IN A MICROFLUIDIC DEVICE

TECHNICAL FIELD

The present invention relates to the field of microfluidic devices and methods for detecting and/or quantifying analytes in fluid samples.

BACKGROUND ART

Developing countries account for 84% of the global population, but spend only 12% of global health expenditure while at the same time carrying 90% of the global diseases burden. As a result of this discrepancy the occurrence of communicable and non-communicable diseases remains very high in developing countries. In 2013 alone, over 8 million people died before reaching the age of 60 from otherwise treatable diseases such as strokes, heart diseases and diabetes as well as the flu, hepatitis and many others. This situation has not markedly improved over the last decade and third world countries are still struggling with a number of health care challenges including accurate diagnosis of e.g. infectious diseases and access to health care facilities. Due to the limited access to healthcare facilities, outpatient diagnosis is key in identifying mild, medium and severe cases that need immediate attention and in some cases warrant quarantine measures. Unfortunately, fully equipped and functional laboratories that have electricity, refrigeration and trained personal are only available in big cities, thus leaving rural communities largely vulnerable and unprotected.

Latest experience has also shown, that similar challenges in the accurate diagnosis of infectious diseases also present themselves in developed countries during pandemic outbreaks. Due to the large number of potentially infected persons in these situations, healthcare facilities are quickly overburdened, and capacities of diagnostic laboratories, even in countries with advanced healthcare systems, have proven to be insufficient.

Lab-on-a-chip technology using microfluidic devices is known for its ability to perform complex fluid handling, sample processing, signal amplification and detection, and is considered one suitable alternative to conduct on site diagnostics assays in point-of-care situation. According to WHO ASSURED criteria and ideal point of care devices needs to be affordable, user-friendly and rapidly provides reliable and robust information to the end-user in the absence of bulky and expensive equipment. In fact, due to the high sensitivity, specificity and accuracy of current point-of-care testing devices, countless lives have already been saved in third world countries by detecting e.g. infections at early stages. For instance, a number of point-of-care devices based on molecular diagnostic assays, lateral flow assay, microfluidics, plasmonic and paper-based devices have been reported for the detection of e.g. viral infections such as HIV, ZIKA, Ebola and dengue. The successful application of point-of-care devices is also reflected in the global market values, which accounted for USD 20.15 Billion in 2017 with a CAGR of 12.4% and is expected to reach USD 57.85 Billion by 2026.

It is the object of the invention to provide means to conduct a cheap, accurate, and quick diagnosis of infectious diseases without the necessity of a full scale laboratory.

SUMMARY OF THE INVENTION

Thus, the present invention relates to a microfluidic device comprising at least one fluid channel comprising at least one inlet. Said at least one fluid channel of the microfluidic device according to the invention is fluidly connected to a first sensor downstream of said at least one fluid inlet, wherein the first sensor comprises at least one sensor cathode and at least one sensor anode formed on an essentially electrically isolating substrate. The sensor cathode and the sensor anode are spaced apart by a gap formed on the electrically isolating substrate, and at least one analyte capturing molecule is immobilized in the gap on the substrate. The at least one capturing molecule is adapted to capture at least one analyte of a fluid sample introduced into the inlet and transported to the first sensor. The microfluidic device comprises at least one second sensor fluidly connected to the fluid channel or to said first sensor, wherein the at least one second sensor comprises at least one sensor cathode and at least one sensor anode formed on an essentially electrically isolating substrate. The sensor cathode and the sensor anode of the second sensor are spaced apart by a gap formed on the electrically isolating substrate, and at least one capture molecule is immobilized in the gap on the substrate, which is adapted to capture at least one analyte of a sample introduced into the inlet and transported to the second sensor. The gap between the sensor cathode and the sensor anode of the at least one second sensor is larger or smaller in size to the gap of the first sensor, and the at least one second sensor is connected to the fluid channel downstream of the first sensor. Larger or smaller means, that the gap between the sensor cathode and the sensor anode of the at least one second sensor is larger or smaller in size compared to the gap of the first sensor. The variation in size between the sensor gaps of the first sensor and the second sensor are not the result of variations, which occur during the production process, but are deliberately chosen to differ from each other in order to achiever different sensitivities and measurement results. Preferably the sensor gaps between the first sensor and the second sensor differ about 5% to 10%. It is also possible to use greater differences in size of the gap like 50% or more.

The microfluidic device according to the present invention is particularly advantageous because it allows to determine the presence and the quantity of an analyte present in a fluid sample. In the course of such analysis the analyte of a fluid sample is captured in the gap of the first and the second sensor by analyte capturing molecules. Thereafter, a second analyte binding molecule labelled with a particle comprising a metal, preferably an inert metal, more preferably gold, is introduced into the microfluidic device and in particular into the sensor. This second molecule binds to the analyte, so that the analyte present in the gap is labelled. In a next step a solution comprising silver is introduced into the microfluidic device and in particular into the sensor. Thereafter, silver dendrites are formed in those gaps where sufficient metal particles are present to bridge the non-conducting gap between the anode and cathode, thus connecting an otherwise interrupted electric circuit.

Another aspect of the present invention relates to a method for detecting and/or quantifying at least one analyte in one or more fluid samples comprising the steps of a) introducing at least one fluid sample into at least one fluid channel or into the first sensor and optionally into the at least one second sensor of a device according to the present invention, b) applying at least one analyte binding molecule to into at least one fluid channel or into the first sensor and optionally into the at least one second sensor of said device, c) applying a silver agent into at least one fluid channel or into the first sensor and optionally into the at least one second sensor of said device, d) applying a current to at least one sensor cathode and at least one sensor anode, and e) detecting and/or determining the current flow between the at least one sensor cathode and the at least one sensor anode.

SHORT DESCRIPTION OF THE FIGURES

FIG. 1 shows an overview of portable and self-powered lab-on-chip system for ultra-low detection of biomarkers combining microfluidics, affinity-based sensors connected to readouts and integrated fuel cells (a microfluidic device of the present invention).

FIG. 2a to FIG. 2c show cross-sectional views of a sensor of the microfluidic device according to FIG. 1; FIG. 2a schematically shows a nano-based immunoassay based on (i) affinity-based detection principal to capture the analyte; FIG. 2b shows labelling using gold nanoparticles (50 nm) modified with secondary antibodies; and FIG. 2c shows signal amplification using silver dendrite. formation to close the gap between the electrodes, resulting in electrical connection of the fuel cell and read out system.

FIG. 3 shows schematic drawings of (i) the working principle of enzymatic fuel cells based on hydrogel-entrapped glucose oxidase and laccase as well as (ii) the equivalent circuit model.

FIG. 4 shows: A) optical analysis of affinity-based assay to determine the best suitable linker chemistry. The absorbance values for different surface modification techniques are shown in graph ±SD; B) schematic drawing of site-specific binding orientation of primary IgG antibodies to the protein A region of the nanocrystalline surface protein (S-layer SbpA/ZZ); C) current-time trace of silver dendrite formation at nanogold labelled needed to form conductive bridges between interdigitated electrode structures.

EMBODIMENTS OF THE INVENTION

Figure 1:
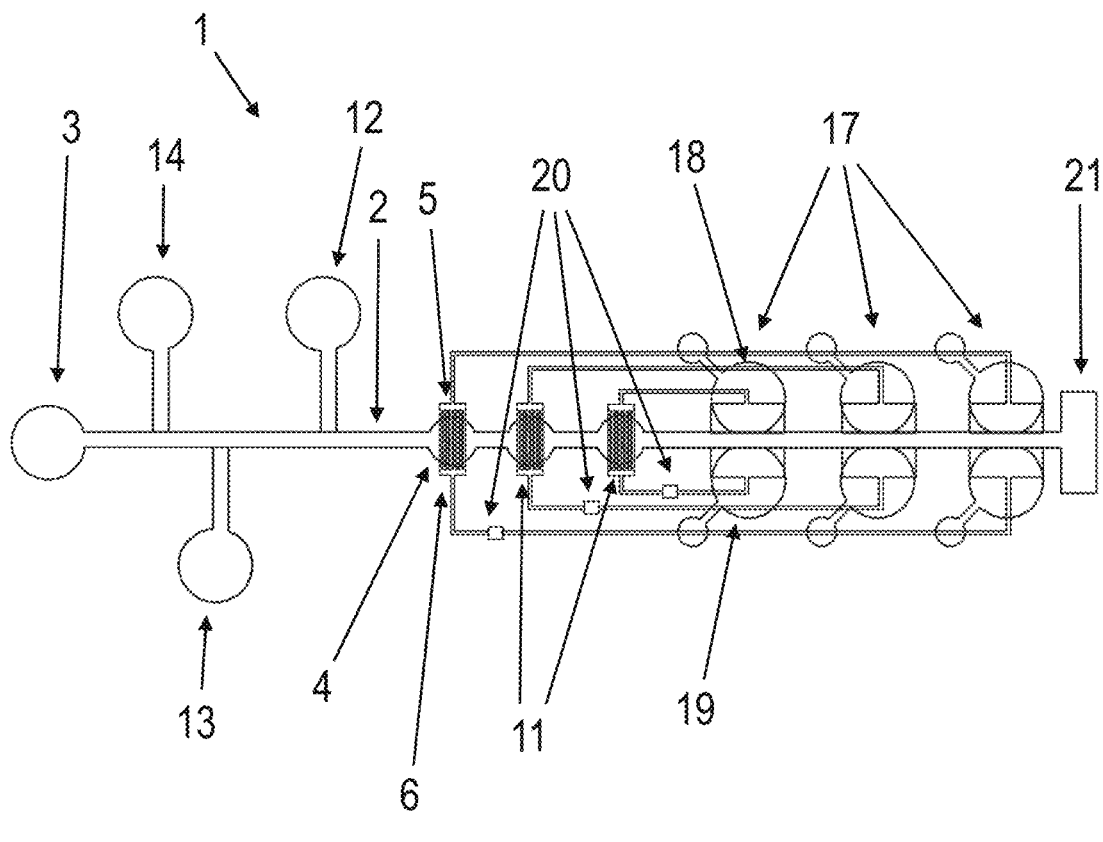

The microfluidic device of the present invention can be produced using methods known in the art. The device can be produced using a polymer or glass as substrate which forms the base of the device. On said substrate the channels are formed and the electrodes, the anodes and the cathodes, are positioned. The substrate as well as the material used to form the channels is substantially electrically isolating. The term "substantially electrically isolating" includes also "electrically isolating".

The microfluidic device of the present invention comprises more than one sensor fluidly connected to the at least one fluid channel. Hence, the microfluidic device according to the invention comprises at least one second sensor fluidly connected to the fluid channel or to said first sensor, wherein the at least one second sensor comprises at least one sensor cathode and at least one sensor anode formed on an essentially electrically isolating substrate, wherein the sensor cathode and the sensor anode are spaced apart by a gap formed on the electrically isolating substrate, and wherein at least one capture molecule is immobilized in the gap on the substrate, which is adapted to capture at least one analyte of a sample introduced into the inlet and transported to the second sensor.

The presence of at least one second sensor is particularly advantageous, because it allows to determine the presence of more than one analyte in a sample at the same time if the analyte capturing molecule immobilizing within the gap of the at least one second sensor is able to bind to and capture another analyte as the first sensor. Furthermore, by selecting a dimension of the gap of the at least one second sensor different from the dimension of the gap of the first sensor, a wider arrange of concentrations of the analyte can be detected by the microfluidic device according to the invention. A quantitative or semi quantitative determination of an analyte within a sample can also be achieved by using different sensors having the same gap size.

According to a preferred embodiment of the microfluidic device according to the invention, the device comprises a first reservoir containing a buffer fluid, a second reservoir containing at least one analyte binding molecule and a third reservoir containing a silver agent, wherein the first reservoir, the second reservoir and the third reservoir are adapted to discharge their respective contents into the fluid channel, into the first sensor, and/or into the second sensor.

By discharging the contents of the first reservoir, the second reservoir and the third reservoir in the fluid channel, the first sensor and/or the at least one second sensor silver bridges are formed in the gap of the sensors, which promote electric conductivity between the cathode and the anode of the sensors as described above.

According to an example which is not part of the invention, the gap between the sensor cathode and the sensor anode of the at least one second sensor is essentially equal in size to the gap of the first sensor.

According to the invention, the gap between the sensor cathode and the sensor anode of the at least one second sensor is larger or smaller in size to the gap of the first sensor, wherein the at least one second sensor is connected to the fluid channel downstream of the first sensor. By this configuration, if the gap of the first sensor is saturated with analyte, the second sensor can be used to detect a wider range of analyte concentrations.

Preferably the sensor cathode and the sensor anode of the first sensor are arranged in an interdigital configuration. The interdigital configuration increases the sensitivity of the sensor.

According to the preferred embodiment, the microfluidic device comprises a power source connectable or connected to the first sensor and/or the at least one second sensor.

In order to apply current to the electrodes of the device of the present invention the electrodes may be connected to an external or to an internal power source. The use of an internal power source is particularly preferred because it allows to use the microfluidic device without any further device.

According to a preferred embodiment of the present invention the power source, preferably the internal power source, comprises a fuel cell comprising a fuel cell cathode and a fuel cell anode, wherein the fuel cell cathode and the fuel cell anode are separated by the fluid channel. This embodiment provides the advantage, that no external power supply is necessary for the operation of the microfluidic device according to the invention.

According to an alternative embodiment, the power source comprises an inductive coupling coil. This provides the advantage of a contactless power transfer.

The microfluidic device according to the invention may comprise a power source which comprises a fuel cell, which is preferably a membraneless fuel cell comprising a fuel cell cathode and a fuel cell anode spaced apart from the fuel cell cathode by a fuel cell gap, and wherein the fuel cell cathode and the fuel cell anode are arranged that the fuel cell gap may be filled with the fluid sample transported via the fluid channel from the inlet to the fuel cell gap, and wherein a material of the fuel cell cathode and a material of the fuel cell anode are selected to generate voltage, when the fuel cell gap is filled with a body fluid. According to this embodiment, an operating voltage of the microfluidic device can be generated directly by using the sample to be analysed.

According to this embodiment the fuel cell cathode and the fuel cell anode may be arranged in one plane, wherein the fluid channel runs over the fuel cell cathode and the fuel cell anode.

The fuel cell cathode and the fuel cell anode may alternatively be arranged on opposite sides of the fluid channel.

The membraneless fuel cell may also comprise multiple fuel cell cathodes and multiple fuel cell anodes, arranged in a parallel or a serial electric circuit.

The fuel cell cathode and the fuel cell anode may comprise a triangular shape with a right angle, and the fuel cell cathode and the fuel cell anode may be arranged with their respective hypotenuses facing each other.

The fuel cell cathode and the fuel cell anode may also comprise a triangular shape with a right angle, and the fuel cell cathode and the fuel cell anode may be arranged with their respective hypotenuses facing each other, wherein the fluid channel runs between the hypotenuses of the fuel cell anode and the fuel cell cathode.

According to the preferred embodiment, the first sensor and/or the at least one second sensor are connected or connectable to a respective sensor readout device. The sensor readout device is preferably connected or connectable to the power source. Advantageously, the sensor readout device comprises LEDs, wherein each sensor of the microfluidic device is connected or connectable to at least one LED.

According to an alternative embodiment, the sensor readout device comprises an active RFID circuitry.

Preferably, the microfluidic device comprises a fluid absorption area connected to the fluid channel at an end of the fluid channel located opposite to the fluid inlet. The fluid absorption area improves the fluid transport rate through the fluid channel. The fluid absorption area may comprise cellulose or derivatives thereof or any suitable material typically used to absorb liquids in test strips.

According to the preferred embodiment, the reservoirs are fluidly connected to the fluid channel between the fluid inlet and the first sensor, the first reservoir being connected upstream of the first sensor, the second reservoir being connected upstream of the first reservoir and the third reservoir being connected upstream of the second reservoir. This configuration ensures, that the fluid contained in the first reservoir reaches the first sensor before the fluid contained in the second reservoir, which reaches the first sensor before fluid contained in the third reservoir.

Preferably the first reservoir, the second reservoir and the third reservoir each comprise a membrane located between the respective reservoir and the fluid channel. The membrane also allows to control the sequence of introduction of the fluids into the fluid channel.

The membrane of the first reservoir is, according to an embodiment of the present invention, thinner than the membrane of the second reservoir, and the membrane of the second reservoir is thinner than the membrane of the third reservoir.

In order to control the flow of fluids, the membranes are preferably adapted to dissolve upon contact with the fluid sample, wherein the membrane of the first reservoir is adapted to dissolve quicker than the membrane of the second reservoir, and the membrane of the second reservoir is adapted to dissolve quicker than the membrane of the third reservoir.

The membrane preferably comprises or consists of a water-soluble material such as cellulose (paper), a polymer or a mineral.

According to an advantageous embodiment, at least one analyte capturing molecule and/or at least one analyte binding molecule is an antibody or a fragment thereof, preferably selected from the group consisting of a polyclonal antibody, monoclonal antibody, chimeric antibody, single chain antibody, a Fab fragment, a Fab' fragment and a F(ab') 2 fragment. It is particularly preferred, that the antibody of fragment thereof is able to bind to a virus protein, preferably to a Corona virus protein, more preferably to a SARS CoV 2 virus protein. The virus protein is preferably an envelope protein, more preferably a spike protein, more preferably a Corona virus spike protein, more preferably a SARS CoV 2 spike protein, more preferably a SARS CoV 2 spike S1 protein.

Furthermore, at least one analyte binding molecule may be labelled with a metal nanoparticle, preferably an inert metal nanoparticle, more preferably with a gold nanoparticle.

The metal nanoparticles used in the present invention may have a diameter of 10 to 100 nm, preferably of 20 to 80 nm, more preferably 30 to 60 nm, more preferably 40 to 60 nm, more preferably approx. 50 nm.

The silver agent may be a silver salt, preferably silver nitrate or commercially available silver enhancement sets.

Another aspect of the present invention relates to a method for detecting and/or quantifying at least one analyte in one or more fluid samples comprising the steps of a) introducing at least one fluid sample into at least one fluid channel or into the first sensor and optionally into the at least one second sensor of a device according to the invention, b) applying at least one analyte binding molecule to into at least one fluid channel or into the first sensor and optionally into the at least one second sensor of said device, c) applying a silver agent into at least one fluid channel or into the first sensor and optionally into the at least one second sensor of said device, d) applying a current to at least one sensor cathode and at least one sensor anode, and e) detecting and/or determining the current flow between the at least one sensor cathode and the at least one sensor anode.

The invention also relates to a membraneless fuel cell comprising a fluid channel with an inlet for introducing a fluid sample into the fluid channel, wherein the fuel cell comprises a fuel cell cathode and a fuel cell anode spaced apart from the fuel cell cathode by a fuel cell gap, and wherein the fuel cell cathode and the fuel cell anode are arranged that the fuel cell gap may be filled with the fluid sample transported via the fluid channel from the inlet to the fuel cell gap, and wherein a material of the fuel cell cathode and a material of the fuel cell anode are selected to generate voltage, when the fuel cell gap is filled with a body fluid.

The fuel cell cathode and the fuel cell anode of the membraneless fuel cell may be arranged in one plane, wherein the fluid channel runs over the fuel cell cathode and the fuel cell anode.

The fuel cell cathode and the fuel cell anode may also be arranged on opposite sides of the fluid channel.

The membraneless fuel cell may also comprise multiple fuel cell cathodes and multiple fuel cell anodes, arranged in a parallel or a serial electric circuit.

The fuel cell cathode and the fuel cell anode may also comprise a triangular shape with a right angle, and the fuel cell cathode and the fuel cell anode may be arranged with their respective hypotenuses facing each other.

The fuel cell cathode and the fuel cell anode may comprise a triangular shape with a right angle, and the fuel cell cathode and the fuel cell anode may be arranged with their respective hypotenuses facing each other, wherein the fluid channel runs between the hypotenuses of the fuel cell anode and the fuel cell cathode.

The present invention also relates to a method of generating voltage using a membraneless fuel cell as described above, characterized by the steps:

providing a body fluid
  introducing the body fluid in the inlet of the membrane-
    less fuel cell.

The invention also relates to a microfluidic device comprising a membraneless fuel cell as described above.

The microfluidic device comprises, according to another, alternative example, at least one fluid channel comprising at least one inlet, wherein said at least one fluid channel is fluidly connected to a first sensor downstream of said at least one fluid inlet, wherein the first sensor comprises at least one sensor cathode and the at least one sensor anode formed on an essentially electrically isolating substrate, wherein the sensor cathode and the sensor anode are spaced apart by a gap formed on the electrically isolating substrate, and wherein at least one analyte capturing molecule is immobilized in the gap on the substrate, wherein the at least one capturing molecule is adapted to capture at least one analyte of a fluid sample introduced into the inlet and transported to the first sensor. According to this example the microfluidic device also comprises a power source connectable or connected to the first sensor and/or the at least one second sensor, wherein the power source comprises a fuel cell comprising a fuel cell cathode and a fuel cell anode, wherein the fuel cell cathode and the fuel cell anode are separated by the fluid channel.

According to a preferred embodiment of this example, the microfluidic device comprises at least one second sensor fluidly connected to the fluid channel or to said first sensor, wherein the at least one second sensor comprises at least one sensor cathode and at least one sensor anode formed on an essentially electrically isolating substrate, wherein the sensor cathode and the sensor anode are spaced apart by a gap formed on the electrically isolating substrate, and wherein at least one capture molecule is immobilized in the gap on the substrate, which is adapted to capture at least one analyte of a sample introduced into the inlet and transported to the second sensor.

Furthermore, in the microfluidic device according to this example the gap between the sensor cathode and the sensor anode of the at least one second sensor preferably varies or is preferably larger or smaller in size to the gap of the first sensor, wherein the at least one second sensor is connected to the fluid channel downstream of the first sensor. Alternatively, the gap between the sensor cathode and the sensor anode of the at least one second sensor is essentially equal in size to the gap of the first sensor.

The microfluidic device of the alternative example comprises preferably a first reservoir containing a buffer fluid, a second reservoir containing at least one analyte binding molecule and a third reservoir containing a silver agent, wherein the first reservoir, the second reservoir and the third reservoir are adapted to discharge their respective contents into the fluid channel, into the first sensor, and/or the second sensor.

In the alternative example of the Microfluidic device the sensor cathode and the sensor anode of the first sensor may be arranged in an interdigital configuration.

The sensor cathode and the sensor anode of the at least one second sensor may also be arranged in an interdigital configuration.

In the alternative example of the microfluidic device the first sensor and/or the at least one second sensor may be connected or connectable to a respective sensor readout device.

Furthermore, the reservoirs may be fluidly connected to the fluid channel between the fluid inlet and the first sensor, the first reservoir being connected upstream of the first sensor, the second reservoir being connected upstream of the first reservoir and the third reservoir being connected upstream of the second reservoir, wherein the first reservoir, the second reservoir and the third reservoir (14) each comprise preferably a membrane located between the respective reservoir and the fluid channel.

At least one analyte capturing molecule and/or at least one analyte binding molecule may be an antibody or a fragment thereof, preferably selected from the group consisting of a polyclonal antibody, monoclonal antibody, chimeric antibody, single chain antibody, a Fab fragment, a Fab' fragment and a F(ab') 2 fragment.

The at least one analyte binding molecule may be labelled with a metal nanoparticle, preferably an inert metal nanoparticle, more preferably with a gold nanoparticle.

The silver agent may be a silver salt, preferably silver nitrate.

The Method for detecting and/or quantifying at least one analyte in one or more fluid samples may also be performed with the microfluidic device according to the alternative example described above, and comprises the steps of a) introducing at least one fluid sample into at least one fluid channel or into the first sensor and optionally into the at least one second sensor of the microfluidic device, b) applying at least one analyte binding molecule to into at least one fluid channel or into the first sensor and optionally into the at least one second sensor of said device, c) applying a silver agent into at least one fluid channel or into the first sensor and optionally into the at least one second sensor of said device, d) applying a current to at least one sensor cathode and at least one sensor anode, and e) detecting and/or determining the current flow between the at least one sensor cathode and the at least one sensor anode.

Within the scope of the present invention, the expression biofuel cell and fuel cell can be used interchangeably. Furthermore, a fuel cell is defined within the scope of the present invention as a fuel cell or as a battery, where electrolyte is supplied by the fluid channel.

Preferred and alternative embodiments of the microfluidic device and the method according to the invention will be explained hereinbelow with reference to the figures.

DETAILED DESCRIPTION OF THE FIGURES

FIG. 1 shows a microfluidic device 1 according to the invention in a preferred embodiment. The microfluidic device 1 comprises at least one fluid channel 2 comprising at least one inlet 3. The microfluidic device depicted in FIG. 1 comprises one fluid channel 2 and one inlet 3. The fluid channel 2 is fluidly connected to a first sensor 4 downstream of said at least one fluid inlet 3. The first sensor 4 comprises at least one sensor cathode 5 and at least one sensor anode 6 formed on an essentially electrically isolating substrate 7. A cross section of the first sensor 4 is provided in FIG. 2a FIG. 2b and FIG. 2c. The sensor cathode 4 and the sensor anode 5 are spaced apart by a gap 8 formed on the electrically isolating substrate 7. At least one analyte capturing molecule 9 is immobilized in the gap 8 on the substrate 7, wherein the at least one capturing molecule 9 is adapted to capture at least one analyte 10 of a fluid sample introduced into the inlet 3 and transported to the first 4 sensor.

Figures 2A, 2B, 2C:
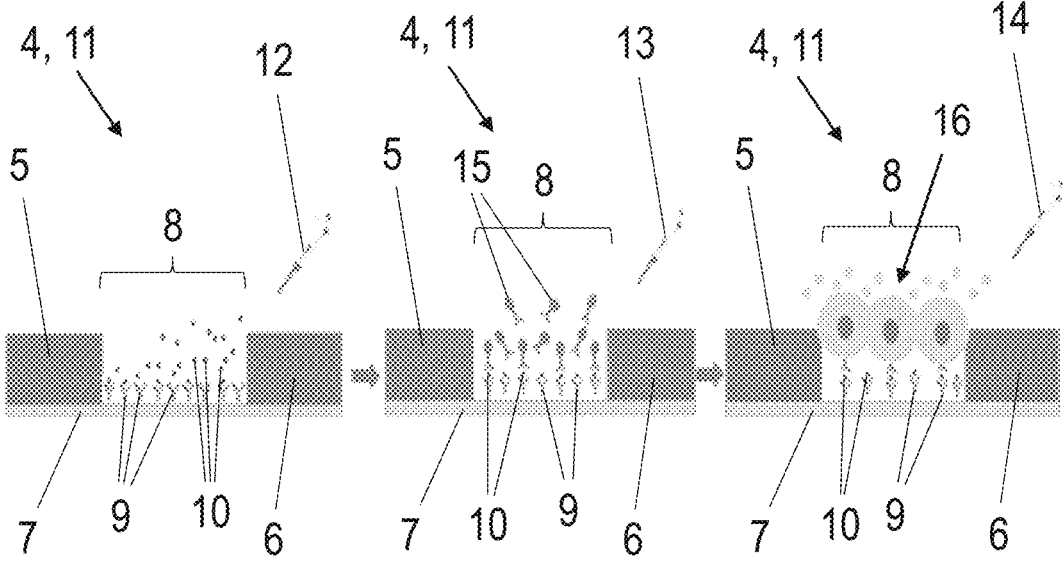

The microfluidic device 1 according to the invention comprises at least one second sensor 11 fluidly connected to the fluid channel 2 or to said first sensor 4. In FIG. 1, two second sensors 11 are provided. The at least one second sensor 11 comprises at least one sensor cathode 5 and at least one sensor anode formed 6 on an essentially electrically isolating substrate 7. The second sensor 11 therefore comprises the same basic construction as the first sensor. The sensor cathode 5 and the sensor anode 6 of the second 11 are spaced apart by a gap 8 formed on the electrically isolating substrate 7, and at least one capture molecule 9 is immobilized in the gap 8 on the substrate 7, which is adapted to capture at least one analyte 10 of a sample introduced into the inlet 3 and transported to the second sensor 11. By providing the second sensor 11, a verification of the results of the first sensor 4 can be achieved. Also by implementing a second sensor 11, different analytes 10 may be detected within the same sample, by choosing a different capturing molecule 9 in the second sensor 11 compared to the first sensor 4. FIG. 2a FIG. 2b and FIG. 2c also serve to illustrate the second sensor 11.

As shown in FIG. 1, the microfluidic device 1 comprises, according to the preferred embodiment, a first reservoir 12 containing a buffer fluid, a second reservoir 13 containing at least one analyte binding molecule 15 and a third reservoir 14 containing a silver agent, wherein the first reservoir 12, the second reservoir 13 and the third reservoir 14 are adapted to discharge their respective contents into the fluid channel 2, into the first sensor 4 and/or into the second sensor 11. Discharging into the first sensor 4 and/or the second sensor 11 is to be interpreted in the meaning, that the contents are discharged directly or indirectly into the gap 8 of the first sensor 4 and/or the second sensor 11. The reservoirs 12, 13, and 14 can either be provided with a fixed connection to the fluid channel 2, as shown in FIG. 1, or as reservoirs 12, 13, 14 which are separate from the fluid channel 2 and can be connected to the fluid channel 2 in order to introduce their respective contents into the fluid channel 2, the first sensor 4 and/or the second sensor 11. According to this embodiment, the reservoirs 12, 13, 14 may be provided for example as syringes or the like. In FIGS. 2a to 2c the reservoirs 12, 13, 14 are depicted as syringes. By introducing the buffer fluid, followed by the analyte binding molecule 15, and at last the silver agent into the fluid channel 2, the first sensor 4, and/or the second sensor 11 silver bridges 16, which are shown in FIG. 2c are formed between the cathode 5 and the anode 6 of the first sensor 4 and/or the second sensor 11 dependent on the amount of captured analyte 10 in the sensor gap 8 by the analyte capturing molecule 9. These silver bridges 16 affect the electric conductivity between the sensor cathode 5 and the sensor anode 6. By measuring the conductivity, the amount of analyte 10 contained in the fluid sample can be derived. According an example which is not part of the present invention, the sensor gap 8 between the sensor anode 5 and the sensor cathode 6 of the at least one second sensor 11 may be chosen to be essentially equal in size to the gap 8 of the first sensor 4. This provides for a verification of the results obtained by the first sensor 4.

According to microfluidic device 1 according to the invention, the gap 8 between the sensor cathode 5 and the sensor anode 6 of the at least one second sensor 11 is larger or smaller in size to the gap 8 of the first sensor 4, wherein the at least one second sensor 11 is connected to the fluid channel 2 downstream of the first sensor 4. By providing different gaps 8 of the first sensor 4 and the second sensor 11, the first sensor 4 and the second sensor 11 can be designed to exhibit different detection limits.

Preferably, the sensor cathode 5 and the sensor anode 6 of the first sensor 4 and/or the second sensor 11 are arranged in an interdigital configuration. The interdigital configuration is shown in FIG. 1. The interdigital configuration increases the surface area of the sensor cathode 5 and the sensor anode 6, which is open to the gap 8, thereby increasing the possibility of bridging the gap 8 by the formation of the silver bridges 16 between the sensor cathode 5 and the sensor anode 6.

According to the preferred embodiment of the microfluidic device 1 according to the invention, the microfluidic device 1 comprises a power source 17 connectable or connected to the first sensor 4 and/or the at least one second sensor 11. In the embodiment shown in FIG. 1 the power source 17 comprises a biofuel cell comprising a fuel cell cathode 18 and a fuel cell anode 19, wherein the fuel cell cathode 18 and the fuel cell anode 19 are separated by the fluid channel 2. The power source shown in FIG. 1 features three biofuel cells, which are each connected to the first sensor 4, or one of the second sensors 11 of the microfluidic device 1 respectively. Therefore, according to the embodiment of FIG. 1, each sensor 4, 11 is connected to a separate biofuel cell. This embodiment provides the advantage, that no external power supply is necessary for the operation of the microfluidic device 1 according to the invention. Alternatively, power sources 17 known in the prior art, for example batteries, accumulators, power grids, and solar panels may be used as power sources.

According to an alternative embodiment, the power source 17 comprises an inductive coupling coil. This provides the advantage of a contactless power transfer.

FIG. 1 shows a sensor readout device 20, wherein the first sensor 4 and/or the at least one second sensor 11 are connected or connectable to a respective sensor readout device 20. The sensor readout device 20 is furthermore connected to the power source 17, wherein the sensor readout device 20 comprises LEDs, and each sensor of the microfluidic device is connected or connectable to at least one LED. In FIG. 1 each of the LEDs has a different colour. A green LED is connected to the first sensor 4, a blue LED is connected to the second sensor 11 downstream of the first sensor 4 and a red LED is connected to the second sensor 11 downstream of the second sensor 11 connected to the blue LED. By choosing the gaps 8 of the first sensor 4, and the two second sensors 11 to increase gradually in the downstream direction of the fluid channel 2, a simple visual readout of the amount of detected analyte 10 in the fluid sample.

In a technologically more sophisticated embodiment of the microfluidic device 1 according to the invention, the sensor readout device 20 comprises an active RFID circuitry, in order to wirelessly transmit the sensor readouts for example to a computer unit like a PC or a portable device like a smartphone, tablet, a laptop or the like.

As shown in FIG. 1, the microfluidic device 1 according to the preferred embodiment of the invention comprises a fluid absorption area 21 connected to the fluid channel 2 at an end of the fluid channel 2 located opposite to the fluid inlet 3. The fluid absorption area 21 may comprise a fluid absorption medium like a sponge or cotton wool. The fluid absorption area 21 increases the rate of fluid transport through the microfluidic device 1.

According to the preferred embodiment, the reservoirs 12, 13, 14 are fluidly connected to the fluid channel 2 between the fluid inlet 3 and the first sensor 4, the first reservoir 12 being connected upstream of the first sensor 2, the second reservoir 13 being connected upstream of the first reservoir 12 and the third reservoir 14 being connected upstream of the second reservoir 13. One possible adaptation of this configuration is shown in FIG. 1. Alternatively, the reservoirs 12, 13 14 could for example be arranged in a straight line and connected by a second fluid channel, which merges into the fluid channel 2 of the microfluidic device 1 between the fluid inlet 3 and the first sensor 4.

Preferably, the first reservoir 12, the second reservoir 13 and the third reservoir 14 each comprise a membrane located between the respective reservoir and the fluid channel 2. The membrane is not shown in the figures. By including such membranes, an automated serial discharge mechanism, which does not require a user intervention or a power supply can be implemented in the device 1 according to the invention. In a preferred embodiment of this variant, the membrane of the first reservoir 12 is thinner than the membrane of the second reservoir 13, and the membrane of the second reservoir 13 is thinner than the membrane of the third reservoir 14. According to this embodiment, the membranes are adapted to dissolve upon contact with the fluid sample, wherein the membrane of the first reservoir 12 is adapted to dissolve quicker than the membrane of the second reservoir 13, and the membrane of the second reservoir 13 is adapted to dissolve quicker than the membrane of the third reservoir 14. The membranes preferably comprise or consist of a water-soluble material as cellulose (paper), a polymer or a mineral.

According to the preferred embodiment, at least one analyte capturing molecule 9 and/or at least one analyte binding molecule 15 is an antibody or a fragment thereof, preferably selected from the group consisting of a polyclonal antibody, monoclonal antibody, chimeric antibody, single chain antibody, a Fab fragment, a Fab' fragment and a F(ab') 2 fragment.

Furthermore, the at least one analyte binding molecule 15 is according to the preferred embodiment labelled with a metal nanoparticle, preferably an inert metal nanoparticle, more preferably with a gold nanoparticle.

Preferably, the silver agent is a silver salt, preferably silver nitrate or commercially available silver enhancement sets.

Figure 3:
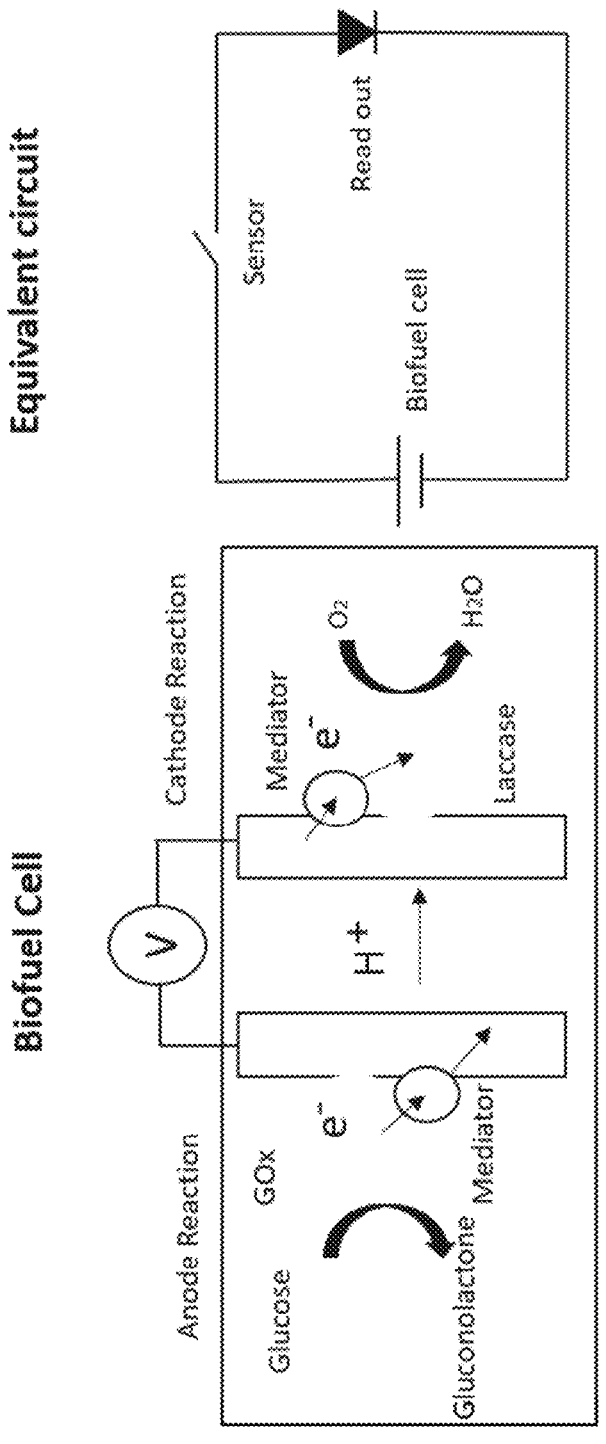
Figure 6:
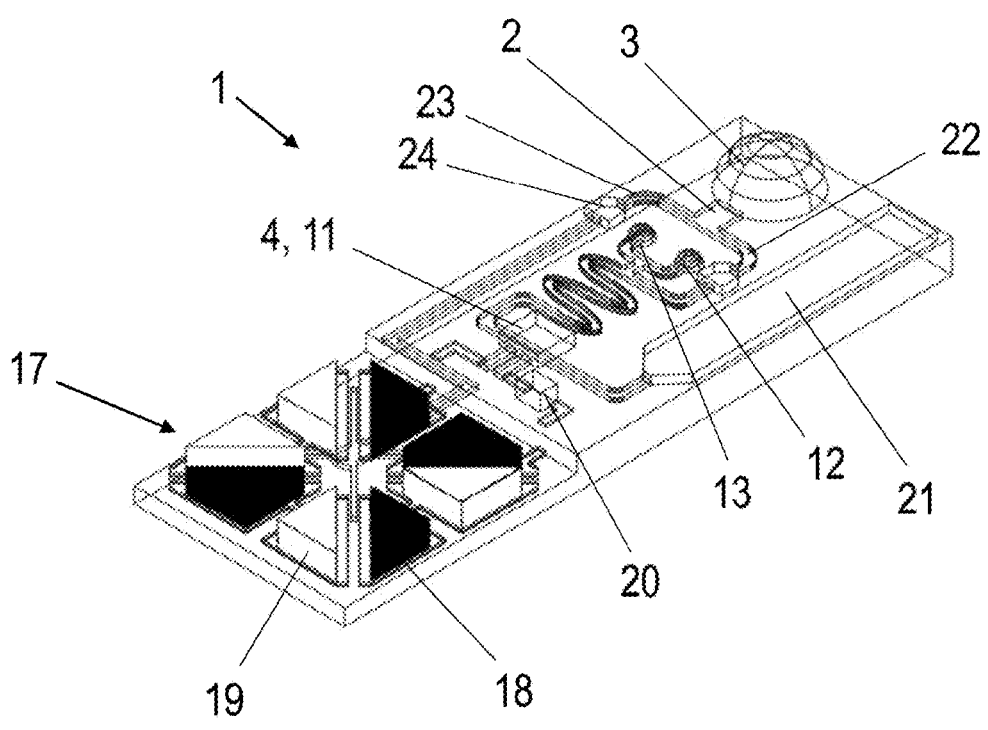
FIG. 6 shows a possible implementation of the microfluidic device according to the invention.

FIG. 6 shows an alternative embodiment of the microfluidic device 1 according to the invention, wherein the fluid channel 2 comprises a first channel 22 and a second channel 23 downstream of the inlet 3. The inlet 3 is shown in FIG. 3 with a drop of sample fluid, which is introduced into the fluid channel. The first channel 22 is connecting the inlet 3 to the reservoirs 12 and 13, which are fluidly connected to the first channel 22 of the fluid channel 2 between the fluid inlet 3 and the first sensor 4. One or more additional reservoirs may also be provided essentially at the position of the reservoirs 12 and 13, like a reservoir 14 as shown in FIG. 1. Essentially at the position, and downstream of the sensor 4, one or more second sensors 11 may also be provided, as disclosed with regards to the embodiment of FIG. 1. Downstream of the sensors 4 and 11, a fluid a fluid absorption area 21 is provided, which may comprise a fluid absorption medium like a sponge or cotton wool.

The second channel 23 connects the inlet 3 with a fuel cell, preferably a membraneless fuel cell, as described hereinabove, which serves as a power source 17 for the sensors 4 and 11. The fuel cell comprises multiple fuel cell cathodes 18 and multiple fuel cell anodes 19, which are arranged in a serial connection. Alternatively the fuel cell cathodes 18 and the fuel cell anodes 19 may also be arranged in a parallel connection. As shown in FIG. 6, the fluid channel 2 introduces the sample into the fuel cell gap 25, thereby providing an electrolyte, in order to generate electricity. The fuel cell is connected to the sensors 4 and 11 in order to provide electricity. A sensor readout device 20 as described hereinabove is also provided in an electrical connection between the fuel cell and the sensors 4 and 11. A conjugate pad 24 may also be provided in a fluid connection with the fluid channel 2 downstream of the inlet 3 and upstream of the fuel cell. The conjugate pad 24 serves to provide additional electrolytes to the fuel cell.

Figure 7:
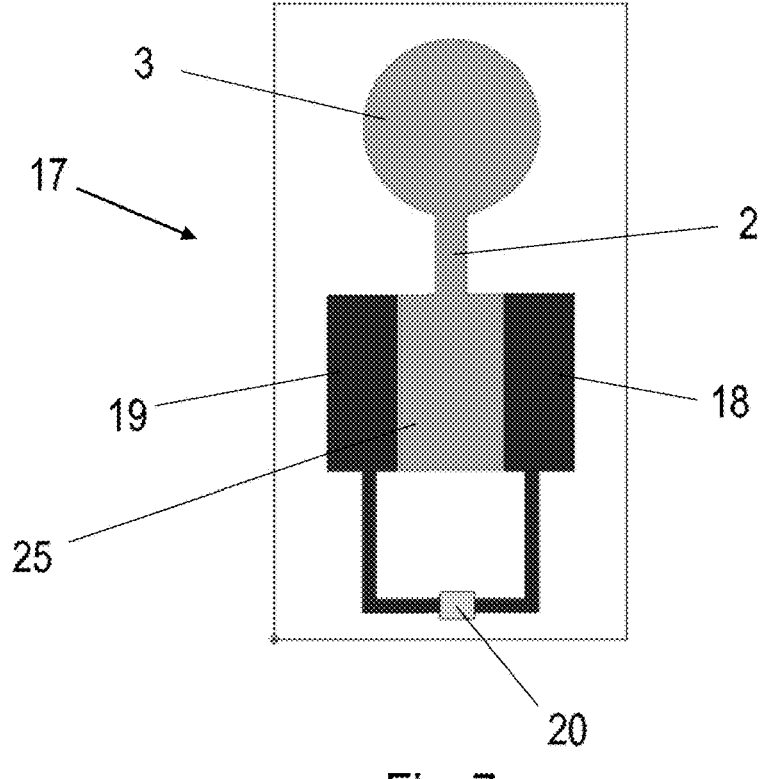
FIG. 7 shows schematic view of a fuel cell which is useable in the microfluidic device according to the invention.
Figure 8:
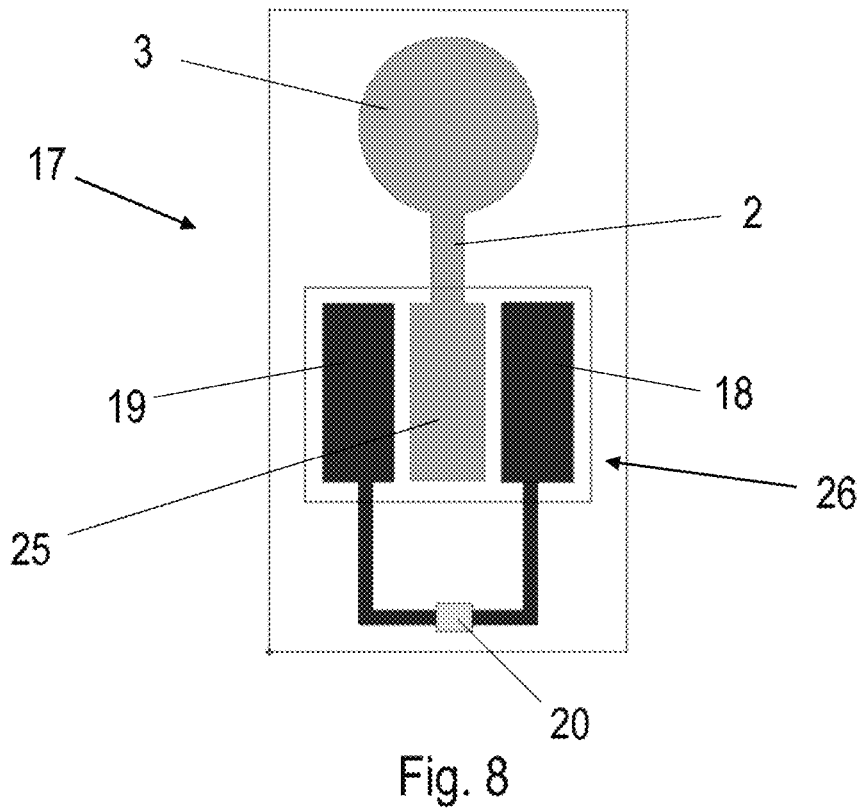
FIG. 8 shows s schematic view of an alternative embodiment of the fuel cell of FIG. 7.

FIG. 7 and FIG. 8 show different embodiments of the fuel cell according to the invention in a schematic view. The power source 17 in form of the fuel cell is designed as described hereinabove, wherein the fuel cell gap 25 between the fuel cell cathode 18 and the fuel cell anode 19 is connected to the inlet 3 via the fluid channel 2. The fuel cell cathode 18 and the fuel cell anode 19 are electrically connected to the sensor readout device 20. In the embodiment displayed in FIG. 8, the fuel cell comprises an additional pad 26.

EXAMPLES

Example 1

Materials and Methods

Fabrication of the Microfluidic Biochips Using Rapid-Prototyping

AutoCAD was used to design the microfluidic channel layout and shadow mask needed for metal deposition to create the electrical leads and electrodes for the biosensor array and biofuel cell. Overall, the microdevice shown in FIG. 1 consisted of (1) a glass bottom substrate containing the microelectrodes, microsensor array and LED; (2) the PDMS microfluidic layer and (3) a glass top cover containing drilled inlet and outlet ports. A Roland Cutter (CAMM-1, GS-24) was used to fabricate the microfluidic channel network and shadow mask by cutting a 250 μm thick PDMS (Polydimethylsiloxane) foil (MVQ Silicones, SIP40HT6240GK0, 25). The PDMS shadow mask was first placed on top of a cleaned glass substrate (sonicating in the presence of a 2% helminex (Hellme analytics) solution followed by isopropanol washing and final rinsing step in deionized water (DI), and electrodes were fabricated by depositing a 50 nm titanium adhesion layer and 80 nm gold layer using a Von Ardenne LSxxx sputter system and cleaned using Harrick Plasma (PDC-002-CE) for 2 minutes prior bonding. The two biofuel cell electrodes (2.5 mm×5 mm) were located in the center of each circular hydrogel chambers (r=3 mm) separated by 1 mm wide microfluidic channel.

Characterization of Redox-Mediated Enzyme Reactions Using Cyclic Voltammetry Potassium hexacyanoferrate (III/II) redox couple (Alfa Aesar, 033357; Fluka, 60279) was used in CV studies to characterize electron transfer reactions from enzymes to the electrodes. A Potentiostat VMP3 (Bio-logic SA) was used determine the potentials required for the maximum electron transfer between the redox couple and enzymes glucose oxidase and laccase. Aliquots of 40 μL from a stock solution consisting 1:2 ratio of potassium hexacyanoferrate (III/II) and 0.5 mg/mL glucose oxidase (Sigma Aldrich, G7141) were mixed with 500 μL and 100 mM f D-Glucose (Sigma Aldrich, G5400) and immediately on top of the gold electrodes. A scan rate of 100 mV/s was applied from Potentiostat VMP3 for a three electrodes (Au WE, Pt-CE and Ag/AgCl Ref) containing electrochemical cell and the resulting peak values were recorded using EC-lab V9.98.

Entrapment of Enzymes and Mediator's in Hydrogels and Biofuel Cell Characterization Both enzymes and mediators were mixed in fibrin hydrogel and allowed to polymerize to yield a stiffness of 1 KPa. Here, 15 μL fibrin and 50 μl 2 U/mL thrombin diluted in CaCl$_2$) was mixed with 20 μL of potassium hexacyanoferrate (III/II) solution (60 mM in PBS (Roche) with (a) 15 μL glucose oxidase (Sigma Aldrich, G7141; 2.5 mg/mL in PBS) for anodic side or (b) 15 μl laccase (Sigma Aldrich, 40452) with concentration of 2.5 mg/ml in PBS (Roche) at the cathodic side. Each enzyme-mediators-fibrin hydrogel mixture was loaded into the respected chambers and sealed with PCR foil, left for 30 min at RG to complete hydrogel polymerization. Performance evaluation of the microfluidic enzymatic biofuel cell was performed in the presence of increasing glucose solutions using cyclic voltammetry at scan rate of 10 mV/s (Potentiostat VMP3).

Biofunctionalization of Capture Regions with Antibodies Using EDC, Ascorbic Acid and S-Layers A) Anti-human IgG (Sigma Aldrich, I9135-2ML) antibodies were diluted in reaction buffer PBS (pH 7.5) to a concentration of 1 mg/mL, centrifuged using Amicon Ultra-0.5 centrifuge and filtered for buffer exchange. Crosslinking Ab to the glass surface was achieved using standard EDC/ sulfo-NHS linker chemistry. In brief 1.1 mg of sulfo-NHS (Thermo Scientific, 24510) was added to 1 mL of the antibody solution and incubated for 1 hour at RT and centrifuged to remove excess of Sulfo-NHS. Next, 1 mL MES buffer (pH 6.0) was added to the Ab solution, centrifuged for buffer exchange followed by sequential addition of 0.4 mg of EDC (Thermo Scientific, 22980) and 1.1 mg of Sulfo-NHS. The reaction mixture was incubated for 15 minutes at RT, centrifuged to remove excess of EDC and Sulfo-NHS and reconstituted in PBS to yield a final Ab concentration of 1 μg/mL. Prior biofunctionalization of the glass bottom substrate (VWR, 631-1577) the glass was rinsed with isopropanol and DI water, plasma treated for two minutes using Harrick Plasma (PDC-002-CE) and incubated for 30 min using a 3% APTES (3-Aminopropyitriethoxysilane) (Sigma Aldrich, 440140-100ML) in absolute ethanol. In the final step, the Ab solution was added, incubated for a period of two hours, following by intensive rinsing with DI water.

B) Ascorbic acid linker protocols are known in the art. In brief, the cleaned and APTES modified glass substrates (see protocol above) was incubated with 0.5 M ascorbic acid (sigma Aldrich, A7506-100G) solution (methanol) for 30 min at RT and rinsed extensively with DI. Next, the modified glass substrate was covered with the anti-human IgG solution (see above) and incubated for 16 h at RT.

C) Establishment of a nanobiointerface using an engineered surface protein layer, rSbpA31-1068/ZZ, is adapted from (Rothbauer, M., et al. (2017) ACS applied materials & interfaces, 9(39), 34423-34434). Here, 2 mg of the lyophilized rSbpA31-1068/ZZ protein were dissolved in 1 ml of 5M GHCL (guanidine hydrochloride) pH 7.2 for 20 min at RT and transferred into dialysis tube (Biomol, 08390.30) with diameter of 6 mm, put inside a flask filled with water and stirred for 30 minutes at 4° C. and centrifuged for 15 minutes at 13000 rpm. Final protein concentration was determined by UV-measurement at 280 nm and aliquots of 100 μL were stored at 4° C. Prior application, the rSbpA31-1068/ZZ protein solution was diluted 1:10 in TRIS-buffer (10 mm CaCl$_2$) in 0.5 mM tris(hydroxymethyl)aminomethane, pH-9), pipetted on top of plasma treated glass substrates and incubated at 40 C over night to allow recrystallization of the rSbpA31-1068/ZZ. After multiple rinsing steps with DI water the anti-human IgG solution (see above) is added and Ab were allowed to bind to the protein A region (ZZ) of the S-layer for a period of 2-4 hours at RT (room temperature). To ensure covalent attachment of the antibody (ab) to the S-layer, in a final step a 10-fold excess solution of the DMP linker (thermo scientific, 21666) in TRIS buffer was added for a period of 30-60 minutes at room temperature.

Absorbance spectroscopy was used to compare the quality of the selected biofunctionalization strategies using Enspire plate reader. Absorption spectroscopy was performed using the wavelength from 320-700 nm with step size of 1 nm.

Affinity-Based and Nanogold-Labelled Sandwich Immunoassay to Detect Human IgG Using Silver Enhancement Chemistry The sandwich bioassay involves first binding of human IgG (Sigma Aldrich, I4506) to the biofunctionalized surface containing anti-human IgG Ab at RT and 10 min, followed by labelling using a secondary anti-human IgG conjugated gold nanoparticle (BBI solutions, BA. GAH40/X) solution (diluted by 1:2 in DI water) for additional 10 min at RT. After rinsing step to remove unbound secondary nanogold labelled Ab, signal enhancement through silver enhancement mixture was added to surface bound gold nanoparticles to form sliver dendrites that electrically connect the interrupted sensor leads. Silver reduction at gold surfaces is accomplished by mixing 1:2 two reagents A and B from a commercially available silver enhancer kit (Sigma Aldrich, SE100). Reduction of silver nitrate to elemental silver took place within 5-10 minutes at RT, followed by removal of the access silver solution using DI or PBS.

Characterization of Silver Dendrite Formation Using Conventional and Conductive-Atomic Force Microscopy To visualize and verify the formation of conductive bridges between interrupted electrode leads, time-resolved AFM in tapping mode was performed using a Nanoscope (viii) multimode scanning probe microscope (Brucker, California). For tapping mode, the single crystal silicone cantilever (NCH, Nanosensors) was used and for cAFM boron doped diamond coated silicone cantilever (Piontprobe CONT, NanoWorld, Switzerland) was used.

Results and Discussion

Design Concept and Characterization of the Self-Powered Lab-On-a-Chip System

The current self-powered lab-on-a-chip design combines biofuel cells, microsensors and display units on a common microfluidic platform to perform sample handling, sensing and readout in remote areas. FIG. 1 shows a picture of the biochip featuring a sample inlet port, three reservoirs including silver reagent, nanogold-labelled secondary antibodies and buffer as well as interdigitated electrode structures acting as sensors and one-way connector switches and enzymatic biofuel cells. The basic principle of the microfluidic biofuel cell and underlying circuit equivalence are shown in FIG. 3, while FIG. 2 reveals the implemented bioassay strategy. An important design criterion of the self-powered lab-on-a-chip is the ability to identify biomarkers and pathogens with ultra-low detection limits. To achieve this goal two strategies are being investigated including (1) optimization of the surface biofunctionalization to increase antibody-antigen binding events (FIG. 2a) and (2) signal amplification using silver enhancement chemistry (FIG. 2c).

Figure 4:
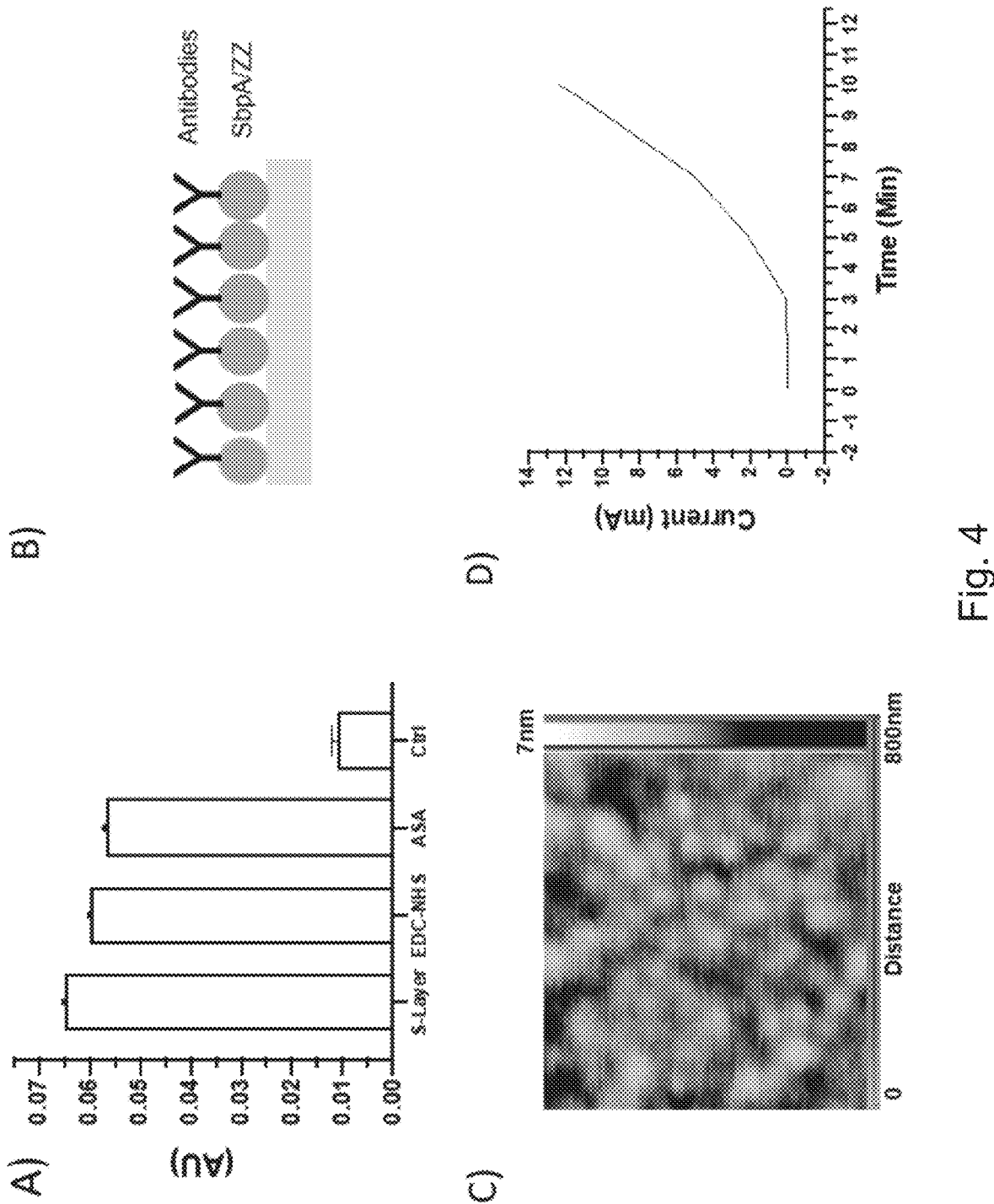

An important step in any affinity-based detection method is the optimization of the biointerface needed to capture, retain and detect the analyte. In total three antibody immobilization strategies including two cross linker chemistries and S-layer technology were initially assessed using absorbance spectroscopy. FIG. 4A shows result from a comparative study, where anti-IgG antibodies were immobilized on 9 cover glasses (n=3) using EDC-NHS and ascorbic acid (ASA) linker chemistry as well as the engineered S-layer SbpA/ZZ. The specific protein A binding sequence for IgG of the S-layer resulted in highest absorbance values of 0.07, followed by EDC-NHS of 0.06 and ASA 0.05 (e.g. controls 0.01). Although all three immobilization protocols yielded similar results, the recombinant S-layer system rSbpA/ZZ was selected for subsequent experiments, because of the preferred orientation of the antibodies at the binding site (see also FIG. 4B), the intrinsic anti-fouling properties and high porosity of the recrystallized rSbpA/ZZ protein layer, thus allowing efficient electron transfer at the electrode surface. This also means that a single immobilization procedure allows the simultaneous attachment of Ab on two different surface materials such as gold electrodes and separating glass substrate. To verify effective S-layer deposition at gold surfaces and Ab binding in the ZZ region AFM and fluorescence assays are performed in subsequent experiments. Results shown in FIG. 4C revealed successful protein recrystallization at gold surfaces and complete coverage over the entire electrode area. In a final step, electrode functionally in the presence of a dual protein surface layer such as rSbpA/ZZ—anti-human IgG was confirmed using cyclic voltammetry.

Following the immobilization optimization of the capture antibody, the ability of the silver enhancement chemistry to form conductive bridges over a 5 µm wide gap is investigated in detail. In particular, silver concentrations and time needed to electrically connect two individual fingers of the interdigitated electrode structures was assessed in subsequent experiments. The S-layer covered the sensing area (5 µm×5 µm) and was incubated with 1 µg/mL of anti-human IgG overnight, followed by the addition of 1 µg/mL human IgG for 30 min at RT, prior addition of anti-human IgG conjugated-gold nanoparticles. The PDMS microwells were thoroughly rinsed between each step with PBS. As a final step, 10 µL aliquots of the silver reagent were pipetted on top of the sensors and current readings were taken at 0, 1, 3, 5, 7 and 10 minutes using a Potentiostat set at 0.3 V. In the absence of the human IgG (negative control), no formation of silver dendrites and current flow was observed. It turned out that a minimum of 3 minutes is needed to obtain measurable currents that increased significantly with reaction times in the presence of gold nanoparticles. The removal of silver reagent by extensively rinsing the sensor area with DI water stopped formation of silver dendrites at each time point. Microscope images taken after 10 min clearly showed the formation of a thick silver layer on top of the sensing area, while reaction times exceeding 30 min resulted in unspecific and spontaneous formation of elementary silver aggregates. To eliminate any unwanted formation of silver aggregates within a reaction time of 10 min, the silver reagent was diluted with DI to lower the concentration of reactive silver nitrate.

Verification of the One-Way Switch Sensing Strategy Using Standard and Conductive Atomic Force Microscopy (AFM)

Figure 5:
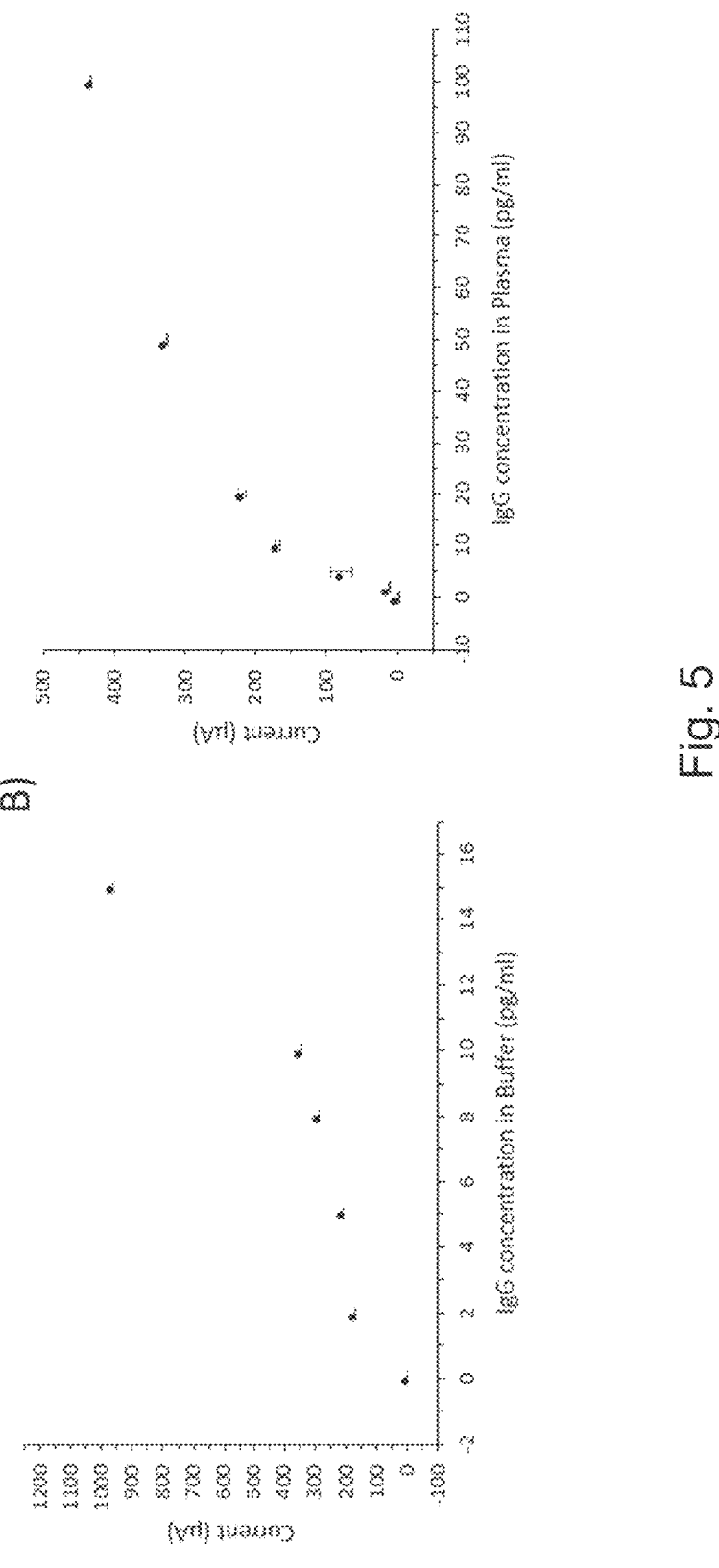
FIG. 5 shows (A) current values obtained in the presence of increasing human IgG concentration diluted in phosphate buffered saline solution (phosphate buffer concentration of 0.01M and a sodium chloride concentration of 0.154M) (n=3) and (B) Electrical signals recorded in the presence of human plasma spiked with decreasing analyte (human IgG) concentrations.

To verify that the above obtained results are, in fact, based on signal generation triggered by the formation of silver dendrites at the gold nanoparticles, time-resolved AFM, XPS and conducting AFM studies are performed to identify (a) the number of gold nanoparticles needed to form a conductive bridge, (b) the materials and layer thicknesses and (c) current flow throw submicron thick silver bridges. Initial AFM images revealed the presence of nanogold labelled secondary Ab located at both the electrode surface and in the gap region between the finger electrodes. In turn, AFM image obtained after silver deposition (5 min) that a layer thickness above the electrodes reached 100 µm in the presence of a fully saturated nanogold surface using 1 µg/mL human IgG and 1 µg/mL nanogold labels. Additional XPS analysis revealed the presence of top silver layer, followed by gold and glass substrates, thus confirming the selective deposition of elementary silver after a short reaction time of 5 min at RT. Next, time-resolved taping mode AFM was conducted to follow the initial formation and growth of silver dendrites from individual gold nanoparticles to create a solid bridge between two electrode fingers. FIG. 5 shows a series of AFM images capturing the onset, growth and formation of a silver bridges. Results of this initial AFM study revealed that at least 2 to 3 gold nanoparticles are needed to reduce enough silver nitrate to bridge the 5 µm gap between two electrode fingers during a 5 min reaction period. In other words, within a reaction time of 5 min the formation of silver dendrites significantly increases the size of gold nanoparticles by a factor of 30 to 50. To further verify whether the formation of individual silver bridges indeed conduct electricity, conductive AFM was employed to measure the current flow between the tip and the surface of the material. cAFM images in the absence and presence of silver bridges confirmed that ability of the silver enhancement chemistry to electrically connect two separated electrode leads, thus acting as one-way switch in the present lab-on-a-chip configuration.

Performance Evaluation of the Self-Powered Lab-On-a-Chip System

The main premise of the application of the silver enhancement chemistry was to obtain ultra-low detection limits. To initially estimate detection limits of the microfluidic one-way sensing switch, decreasing concentrations of IgG from 15 pg/mL to 2 pg/mL in buffer and human plasma samples were investigated. For instance, FIG. 5A shows current readings obtained from 30 interdigitated electrode structures located with a 6 mm long and 400 μm microfluidic channels connected to an external readout. While averaged current values over a measurement period of 4 min already resulted in 172±0.9 μA in the presence of 2 pg/mL IgG concentration, a non-linear signal behavior in the presence of increasing IgG concentration was found. This means that the LOD of our current bioassay is 48-times lower than commonly achieved by commercial ELISA kits with approx. 100 μg/mL. To further evaluate the bioassay performance over a wider range of IgG concentrations, human plasma samples were spiked with IgG. FIG. 5B shows current readings in the presence of 2, 5, 10, 50 and 100 pg/mL IgG resulting in 11.9±0.2, 79±12, 168±2, 220±5, 326±1.6, 433±0.7 μA, respectively. Interestingly, despite a 14-fold current decrease from 172 μA down to 12 μA in the presence of human plasma, the 2 pg/mL IgG was readily detected by the lab-on-a-chip. Interestingly, a linear signal increase up to 20 pg/mL followed by the establishment of a current plateau after 100 pg/mL IgG was obtained, indicating that a saturation in the presence of sufficient conducting bridges. In a final experiment, the integrated self-powered lab-on-a-chip consisting of microfluidic biofuel cells connected to the one-way sensing switch and external readout (Ohmmeter) were challenged against IgG spiked plasma and whole blood samples. While whole blood samples failed to produce any measurable currents, 10 μL aliquots of the 10, 20 and 30 pg/mL spiked human plasma samples yielded 12.5 μA, 18.3 μA and 29.4 μA.

Example 2

Materials and Methods
Fabrication Well Array

Microscope slides were first cleaned by submerging them in a 2% Hellmanex® III solution and placing them in an ultrasonic bath for 5 minutes. Then, the solution was discarded and exchanged with isopropanol and later water, each for 5 minutes in the ultrasonic bath. The slides were first dried with pressurized air and then in the oven at 80° C. for 1 hour.

For the well array, three polydimethylsiloxane (PDMS) layers were bonded on glass. Therefore, the wells with a diameter of 3 mm were cut in a PDMS sheet using a cutting plotter CAMM-1 GS-24 from Roland DG. Cut-outs were removed using tweezers and layers bonded on top of each other using a Plasma Cleaner PDC-002-CE from Harrick Plasma. The first PDMS layer was bonded on a clean microscope slide and the following layers on PDMS. Bonding was strengthened by placing the chip in the oven for 15 minutes.
Immobilization Methods
Adsorption Using adsorption as immobilization method for antibodies, no further surface modification of the cleaned microscope slides was performed. An Alexa Fluor 488 goat anti-rat IgG antibody was diluted in PBS to obtain 3 different concentrations (1, 10, 100 μg/ml) and 5 μl added in each well. The antibody incubated for 1 hour and was discarded afterwards. The wells were washed with wash buffer (0.05% Tween™ 20 in PBS) before imaging.
Covalent Binding For covalent binding of the antibody to the glass surface, (3-Mercaptopropyl)-trimethoxy-silane (3-MPS) was diluted in absolute ethanol to obtain a final concentration of 0.56 mg/ml. The cleaned microscope slide with the wells (prepared as described in 1) were activated with plasma treatment. Then, 10 μl 3-MPS solution was added to each well and incubated for 30 minutes. Meanwhile N-γ-maleimi-dobutyryl-oxysuccinimide ester (GMBS) was dissolved in DMSO to obtain a stock solution of 100 mg/ml, which was further diluted in ethanol to a final concentration of 0.56 mg/ml.

After the 3-MPS incubation, the wells were washed with ethanol. 10 μl of the prepared GMBS solution was added and incubated for another 35 minutes. Afterwards, wells were washed with ethanol and PBS and finally, the antibody solution could be incubated as described above under Absorption.
Protein G The preparation of the wells is the same as described above (Covalent binding), but instead of immobilizing the antibody covalently, protein G was added with a concentration of 1 mg/ml for 1.5 hours. Afterwards, wells were washed with wash buffer (0.05% Tween™ 20 in PBS) and different antibody concentrations as described above (Absorption) added.
Sandwich ELISA on Glass Substrate Capture antibodies against Spike S1 protein of SARS CoV 2 were immobilized using the method described above (Covalent binding). After immobilization, 5 μl Spike S1 protein was incubated for 30 minutes and wells washed afterwards. To finalize the sandwich, 5 μl biotinylated detection antibodies against Spike S1 protein were incubated for 30 minutes. The wells were washed with wash buffer and 10 μl horseradish peroxides (HRP) conjugated with streptavidin added. Finally, after 30 minutes incubation and washing the wells, 10 μl 3,3',5,5'-Tetramethylbenzidin (TMB) substrate was added and incubated for another 15 minutes. The enzymatic reaction was stopped with 0.18 M $H_2SO_4$ and the wells analyzed using a plate reader.
Sandwich ELISA on Electrodes The first steps until detection antibody incubation are the same as described above (Sandwich ELISA on glass substrate), but performed on electrodes and using a decreased incubation time of 15 minutes. Then, instead of HRP/streptavidin, streptavidin labelled gold nanoparticles were used. In a final step, silver enhancement solution was added for 10 minutes to enhance the size of the gold nanoparticles.

Figure 9:
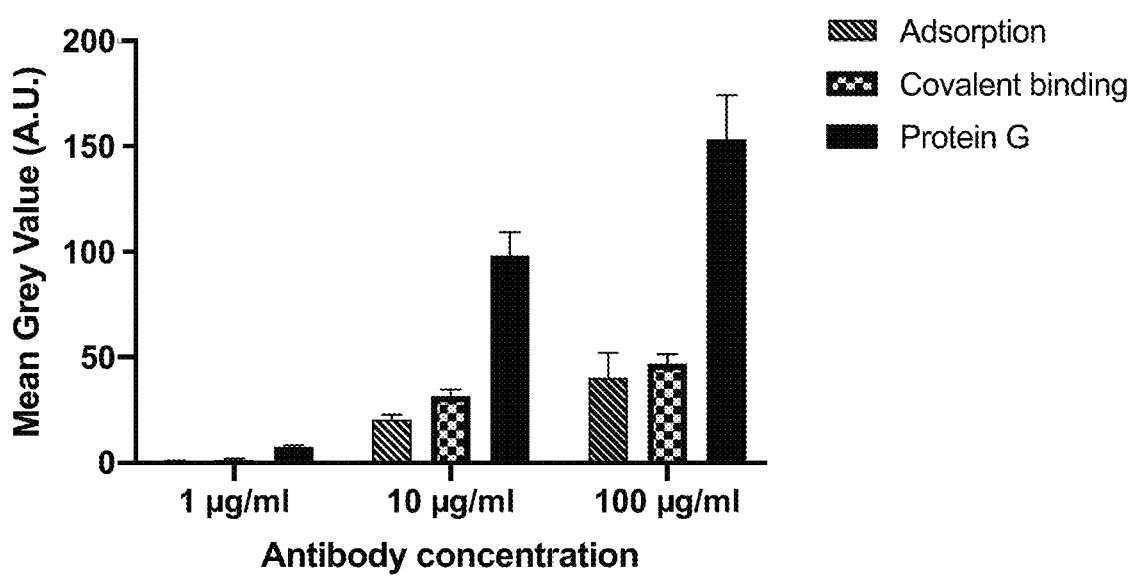
FIG. 9 shows a comparison of the binding of antibodies on glass using various methods for immobilisation.

Commercially available electrodes with a gap of 5 μm were used.
Results and Discussion The commercially available electrodes employed in this example use glass as substrate and therefore different antibody immobilization methods for glass substrate were tested. The results (FIG. 9) show that the oriented immobilization using protein G showed the best results. But also covalent binding shows an increasing signal with higher antibody concentrations. As a result, these methods should be suitable for immobilization the antibodies on glass.

Figure 10:
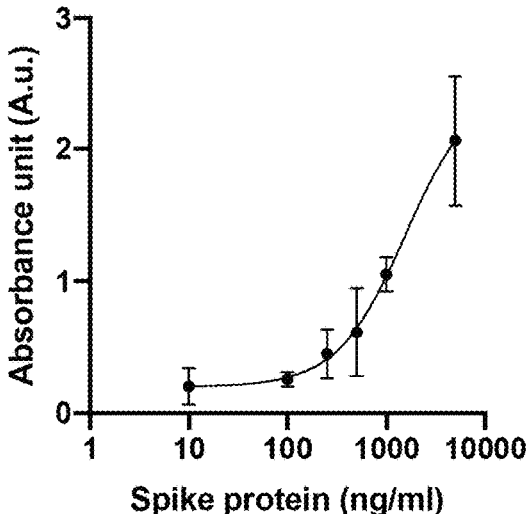
FIG. 10 shows the concentration dependent increase of the absorbance using the bioassay according to example 2.

The bioassay in this lab-on-a-chip platform is similar to a sandwich ELISA. But instead of an enzymatic read-out, the detection antibody is labelled with a gold nanoparticle. To show that sandwich assembly works on glass substrate, a sandwich ELISA was performed using the well array. FIG. 10 shows the concentration dependent increase of the absorbance. Therefore, the sandwich assay works and can be used for the assay on the electrodes.

Figure 11:
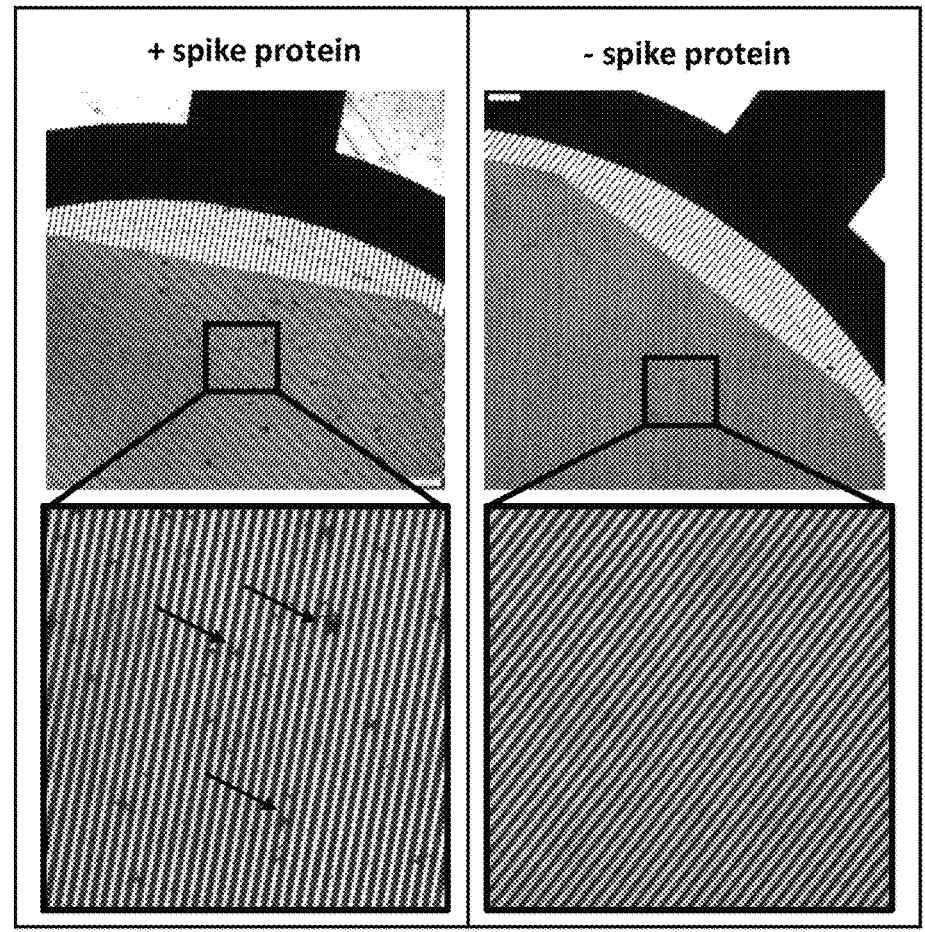
FIG. 11 shows the bridging of the electrodes of a sensor of the present invention in the presence of the SARS-COV 2 spike protein (see example 2).

Instead of the enzymatic read-out, streptavidin labelled gold nanoparticles were used. To enhance these gold nanoparticles, commercially available silver enhancement was added. After the enhancement, spots are visible in the microscope, which indicate the bridging of the electrodes (FIG. 11) in the presence of spike protein.

The invention claimed is:

1. A microfluidic device (1) comprising: at least one fluid channel (2) comprising at least one inlet (3), wherein said at least one fluid channel (2) is fluidly connected to a first sensor (4) downstream of said at least one fluid inlet (3), wherein the first sensor (4) comprises at least one sensor cathode (5) and at least one sensor anode (6) formed on an electrically isolating substrate (7), wherein the sensor cathode (5) and the sensor anode (6) are spaced apart by a gap (8) formed on the electrically isolating substrate (7), and wherein at least one analyte capturing molecule (9) is immobilized in the gap (8) on the substrate (7), wherein the at least one capturing molecule (9) is adapted to capture at least one analyte (10) of a fluid sample introduced into the inlet (3) and transported to the first sensor (4), wherein the microfluidic device (1) comprises at least one second sensor (11) fluidly connected to the fluid channel (2) or to said first sensor (4), wherein the at least one second sensor (11) comprises at least one sensor cathode (5) and at least one sensor anode (6) formed on the electrically isolating substrate (7), wherein the sensor cathode (5) and the sensor anode (6) are spaced apart by a gap (8) formed on the electrically isolating substrate (7), and wherein at least one capture molecule (9) is immobilized in the gap (8) on the substrate (7), which is adapted to capture at least one analyte (10) of a sample introduced into the inlet (3) and transported to the second sensor (11), wherein the gap (8) between the sensor cathode (5) and the sensor anode (6) of the at least one second sensor (11) varies in size compared to the gap (8) of the first sensor (4), wherein the at least one second sensor (11) is connected to the fluid channel (2) downstream of the first sensor (4).

2. A membraneless fuel cell comprising: a fluid channel (2) with an inlet (3) for introducing a fluid sample into the fluid channel (2), wherein the fuel cell comprises a fuel cell cathode (18) and a fuel cell anode (19) spaced apart from the fuel cell cathode (18) by a fuel cell gap (25), and wherein the fuel cell cathode (18) and the fuel cell anode (1) are arranged that the fuel cell gap (25) may be filled with the fluid sample transported via the fluid channel (2) from the inlet (3) to the fuel cell gap (25), and wherein a material of the fuel cell cathode (18) and a material of the fuel cell anode (1) are selected to generate voltage, when the fuel cell gap (25) is filled with a body fluid, wherein the fuel cell cathode (18) and the fuel cell anode (1) are arranged in one plane, wherein the fluid channel (2) runs over the fuel cell cathode (18) and the fuel cell anode (19).

3. The membraneless fuel cell according to claim 2, wherein the membraneless fuel cell comprises multiple fuel cell cathodes (18) and multiple fuel cell anodes (19), arranged in a parallel or a serial electric circuit.

4. The membraneless fuel cell according to claim 2, wherein the fuel cell cathode (18) and the fuel cell anode (19) comprise a triangular shape with a right angle, and the fuel cell cathode (18) and the fuel cell anode (19) are arranged with their respective hypotenuses facing each other.

5. The membraneless fuel cell according to claim 2, wherein the fuel cell cathode (18) and the fuel cell anode (19) comprise a triangular shape with a right angle, and the fuel cell cathode (18) and the fuel cell anode (19) are arranged with their respective hypotenuses facing each other, wherein the fluid channel (2) runs between the hypotenuses of the fuel cell anode (19) and the fuel cell cathode (18).

6. A method of generating voltage using a membraneless fuel cell according to claim 2, comprising the steps of:
   providing a body fluid; and
   introducing the body fluid in the inlet (3) of the membraneless fuel cell.

7. A microfluidic device comprising a membraneless fuel cell according to claim 2.

8. The microfluidic device (1) according to claim 1, wherein the device (1) comprises a first reservoir (12) containing a buffer fluid, a second reservoir (13) containing at least one analyte binding molecule (15) and a third reservoir (14) containing a silver agent, wherein the first reservoir (12), the second reservoir (13) and the third reservoir (14) are adapted to discharge their respective contents into the fluid channel (2), into the first sensor (4), and/or the second sensor (11).

9. The microfluidic device (1) according to claim 8, wherein the reservoirs (12, 13, 14) are fluidly connected to the fluid channel (2) between the fluid inlet (3) and the first sensor (4), the first reservoir (12) being connected upstream of the first sensor (4), the second reservoir (13) being connected upstream of the first reservoir (12) and the third reservoir (14) being connected upstream of the second reservoir (13).

10. The microfluidic device (1) according to claim 9, wherein the first reservoir (12), the second reservoir (13) and the third reservoir (14) each comprise a membrane located between the respective reservoir (12, 13, 14) and the fluid channel (2).

11. The microfluidic device (1) according to claim 8, wherein the at least one analyte binding molecule (15) is labelled with a metal nanoparticle.

12. The microfluidic device (1) according to claim 11, wherein the metal nanoparticle is an inert metal nanoparticle.

13. The microfluidic device (1) according to claim 11, wherein the metal nanoparticle is a gold nanoparticle.

14. The microfluidic device (1) according to claim 8, wherein the silver agent is a silver salt.

15. The microfluidic device (1) according to claim 14, wherein the silver salt is silver nitrate.

16. The microfluidic device (1) according to claim 1, wherein the sensor cathode (5) and the sensor anode (6) of the first sensor (4) are arranged in an interdigital configuration.

17. The microfluidic device (1) according to claim 1, wherein the sensor cathode (5) and the sensor anode (6) of the at least one second sensor (11) are arranged in an interdigital configuration.

18. The microfluidic device (1) according to claim 1, wherein the microfluidic device (1) comprises a power source (17) connectable or connected to the first sensor (4) and/or the at least one second sensor (11).

19. The microfluidic device (1) according to claim 18, wherein the power source (17) comprises an inductive coupling coil.

20. The microfluidic device (1) according to any of claims 1 or 8 to 19, wherein the first sensor (4) and/or the at least one second sensor (11) are connected or connectable to a respective sensor readout device (20).

21. The microfluidic device (1) according to claim 19, wherein the wherein the power source (17) comprises a fuel cell, which is a membraneless fuel cell comprising a fuel cell cathode (18) and a fuel cell anode (19) spaced apart from the fuel cell cathode (18) by a fuel cell gap (25), and wherein the fuel cell cathode (18) and the fuel cell anode (19) are arranged that the fuel cell gap (25) may be filled with the fluid sample transported via the fluid channel (2) from the inlet (3) to the fuel cell gap (25), and wherein a material of the fuel cell cathode (18) and a material of the fuel cell anode (19) are selected to generate voltage, when the fuel cell gap (25) is filled with a body fluid.

22. The microfluidic device (1) according to claim 21, wherein the fuel cell cathode (18) and the fuel cell anode (19) are arranged in one plane, wherein the fluid channel (2) runs over the fuel cell cathode (18) and the fuel cell anode (19).

23. The microfluidic device (1) according to claim 22, wherein the fuel cell cathode (18) and the fuel cell anode (19) comprise a triangular shape with a right angle, and the fuel cell cathode (18) and the fuel cell anode (1) are arranged with their respective hypotenuses facing each other.

24. The microfluidic device (1) according to claim 21, wherein the fuel cell cathode (18) and the fuel cell anode (19) are arranged on opposite sides of the fluid channel (2).

25. The microfluidic device (1) according to claim 21, wherein the membraneless fuel cell comprises multiple fuel cell cathodes (18) and multiple fuel cell anodes (19), arranged in a parallel or a serial electric circuit.

26. The microfluidic device (1) according to claim 21, wherein the fuel cell cathode (18) and the fuel cell anode (1) comprise a triangular shape with a right angle, and the fuel cell cathode (18) and the fuel cell anode (19) are arranged with their respective hypotenuses facing each other, wherein the fluid channel (2) runs between the hypotenuses of the fuel cell anode (18) and the fuel cell cathode (19).

27. The microfluidic device (1) according to claim 1, wherein at least one analyte capturing molecule (9) and/or at least one analyte binding molecule (15) is an antibody or a fragment thereof.

28. The microfluidic device (1) according to claim 27, wherein the antibody or fragment thereof is selected from the group consisting of a polyclonal antibody, monoclonal antibody, chimeric antibody, single chain antibody, a Fab fragment, a Fab' fragment, and a F (ab') 2 fragment.

29. A method for detecting and/or quantifying at least one analyte (10) in one or more fluid samples comprising the steps of:

a) introducing at least one fluid sample into at least one fluid channel (2) or into the first sensor (4) and optionally into the at least one second sensor (11) of a device according to claim 1, b) applying at least one analyte binding molecule (15) to into at least one fluid channel (2) or into the first sensor (4) and optionally into the at least one second sensor (11) of said device, c) applying a silver agent into at least one fluid channel (2) or into the first sensor (4) and optionally into the at least one second sensor (11) of said device, d) applying a current to at least one sensor cathode (5) and at least one sensor anode (6), and e) detecting and/or determining the current flow between the at least one sensor cathode (5) and the at least one sensor anode (6).

* * * * *